United States Patent [19]

Teng et al.

[11] 4,022,053
[45] May 10, 1977

[54] PROJECTILE GUIDE TRACK

[75] Inventors: Robert N. Teng, Huntington Beach; William B. Covey, Long Beach, both of Calif.

[73] Assignee: The United States of America as represented by the Secretary of the Air Force, Washington, D.C.

[22] Filed: Sept. 30, 1975

[21] Appl. No.: 618,094

[52] U.S. Cl. .................................... 73/12; 73/167
[51] Int. Cl.$^2$ .................................... G01N 3/30
[58] Field of Search .................. 73/167, 11, 12; 193/2 R; 89/1.816, 1.819

[56] References Cited
UNITED STATES PATENTS

| | | |
|---|---|---|
| 2,478,774 | 8/1949 | Meinel ........................ 89/1.816 X |
| 2,813,422 | 11/1957 | Schuessler ........................ 73/167 |
| 2,817,272 | 12/1957 | Gunder ........................ 89/1.816 X |
| 3,673,916 | 7/1972 | Wittholz ........................ 89/1.816 |
| 3,678,745 | 7/1972 | Teng ........................ 73/167 |
| 3,718,041 | 2/1973 | Jones et al. ........................ 73/167 |

*Primary Examiner*—S. Clement Swisher
*Attorney, Agent, or Firm*—Joseph E. Rusz; Jacob N. Erlich

[57] ABSTRACT

A projectile guide track having a plurality of track assemblies in aligned relationship with one another. Each track assembly contains fixedly spaced rails for supporting a projectile during flight while undergoing testing in a ballistic range. Precision machining allows for a plurality of different sized rails to be used with a plurality of track assemblies thereby accommodating projectiles of various dimensions.

4 Claims, 3 Drawing Figures

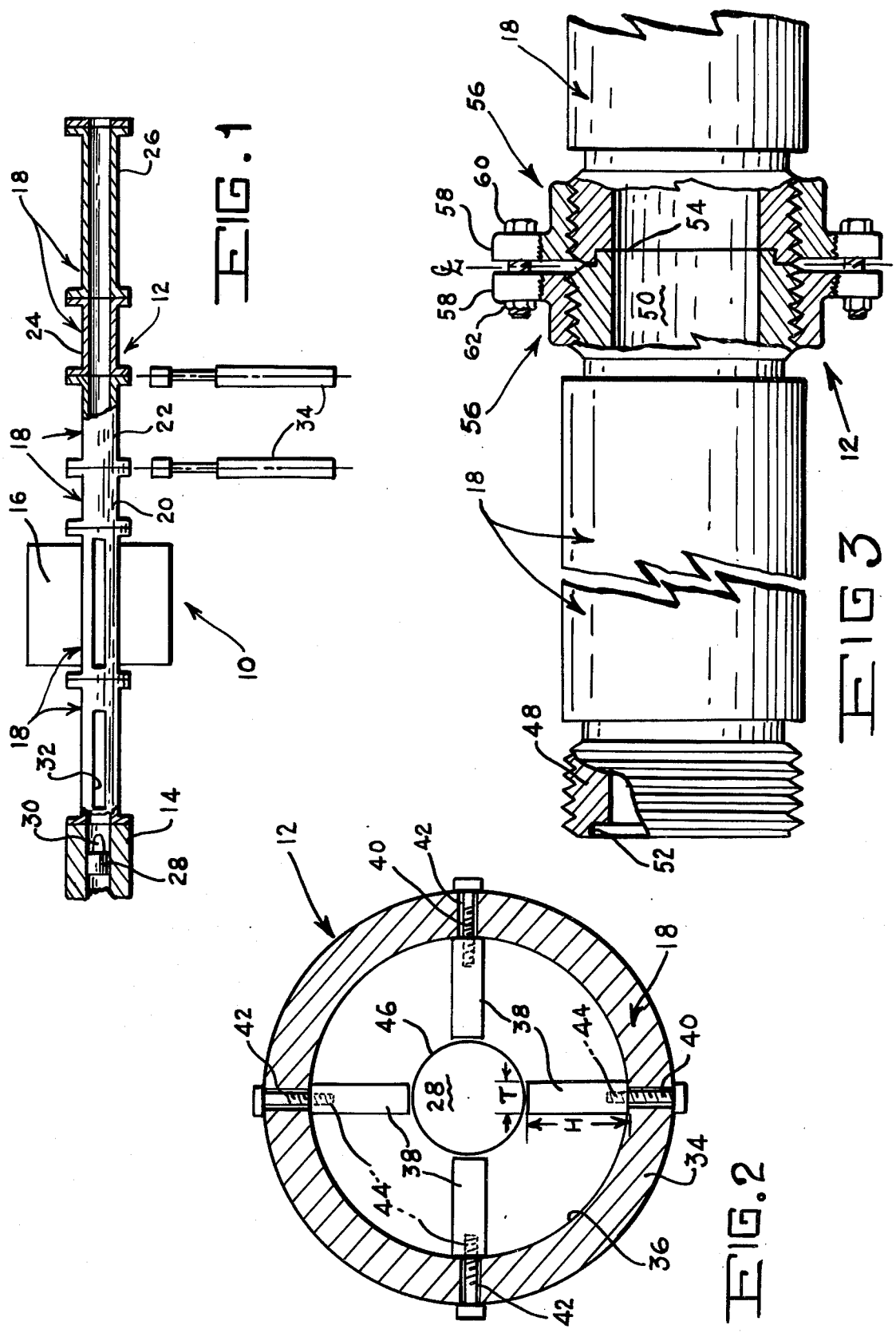

PROJECTILE GUIDE TRACK

STATEMENT OF GOVERNMENT INTEREST

The invention described herein may be manufactured and used by or for the Government for governmental purposes without the payment of any royality thereon.

BACKGROUND OF THE INVENTION

This invention relates generally to projectile testing and deceleration apparatus, and, more particularly, to the projectile guide tracks used therewith.

A ballistic or test range as used in conjunction with this invention is a scientifically oriented artillery-like device for accelerating projectiles to high velocities for the purpose of studying free-flight and impact phenomena. A small test specimen of the desired size and configuration is mounted on a sabot or projectile which adapts the specimen to the gun barrel. The rapidly expanding gases of an explosive charge behind the sabot sends it through a simulated environment chamber where it is subjected to rain, dust or other test material. Muzzle velocities generally attain a maximum of 30,000 feet per second and projectile sizes vary up to 1.5 inches in diameter or larger. For tests specifically conducted to study impact, the specimens are directed into a target and in the process are either destroyed or heavily distorted. In free-flight tests, it has been highly desirable to recover the specimens for analysis of the flight effects.

One problem area encountered in the ballistic ranges of the past has been in the guide rails for the conduits used therewith. These rails were held in place inside steel casings by means of screws, clevis bolts and aligning bulkheads. Manual adjustment of the rails to the exact projectile outside diameter was required to allow smooth passage of the projectile through the ballistic range. Adjustment was arduous, time consuming and frequent, contributing to an inefficient operation and potential model failure.

SUMMARY OF THE INVENTION

This invention sets forth a projectile guide track or rail system which overcomes all the problems encountered in the past and as set forth in detail hereinabove.

The projectile guide track or rail system of this invention is incorporated within a conduit, casing or tube which can be readily used with a conventional ballistic range of the type described hereinabove. The guide track is made up of fixed spaced track assemblies of four rails thereby eliminating manual adjustment of the rails to the projectile outside diameter. The casing, or main load bearing member, is a straight, high strength steel tube with a precision honed inside diameter. The four rails are steel bars, ground to precision height and width which are attached to the casing by means of screws inserted through clearance holes in the casing from the outside and screwed into tapped holes in the rails. Interrail spacing to exact projectile outside diameter is therefore a function of casing inside diameter and the rails height and thickness.

The casing of the guide track of this invention is manufactured in a length that is convenient for the grinding and honing processes necessary to the fabrication of the component parts. Because of the size limitation of grinding and honing facilities, ten feet is a practical length. Since projectile recovery systems longer than ten feet may be desirable, the guide track of this invention is capable of using two or more assemblies bolted together.

The two adjacent track assemblies are secured together such that their axes are in exact alignment. The adjacent track assemblies are held together mechanically be means of a threaded section and an internally threaded flanged ring screwed on the threaded section on adjacent track assemblies. The rings are then held together with bolts through the holes provided. With these provisions for alignment and attachment track assembly test sections of any length can be assembled and the various component track assemblies can be rotated to any angle.

It is therefore an object of this invention to provide a projectile guide track which is of fixed spacing and therefore requires no manual adjustments.

It is another object of this invention to provide a projectile guide track capable of being constructed of any length.

It is still another object of this invention to provide a projectile guide track in which the rails thereof can be interchanged without resort to realignment.

It is a further object of this invention to provide a projectile guide track in which the track assemblies can be rotated to any angle.

It is still a further object of this invention to provide a projectile guide track which is economical to produce, and which utilizes conventional, currently available components that lend themselves to standard mass producing manufacturing techniques.

For a better understanding of the present invention together with other and further objects thereof reference is made to the following description taken in conjunction with the accompanying drawing and its scope will be pointed out in the appended claims.

DESCRIPTION OF THE DRAWING

FIG. 1 is a schematic representation, shown partly in cross section, of a ballistic test range which incorporates therein the projectile guide track of this invention;

FIG. 2 is an end view taken partly in cross-section of the projectile guide track of this invention; and FIG. 3 is a side elevational view, shown partly in cross-section, of a pair of track assemblies of the projectile guide track of this invention shown joined together.

DETAIL DESCRIPTION OF THE PREFERRED EMBODIMENT

Reference is now made to FIG. 1 of the drawing which best shows the ballistic test range 10 with which the projectile guide track 12 of this invention finds its main utility. Ballistic range 10 is generally made up of a guide track 12, a light-gas gun 14 and a test environment 16. The guide track 12 is composed of a plurality of track assemblies 18, with each assembly 18 having an independent function. For example, assembly 18 may be mounted within test environment 16 or form a transition to recovery tube 20, a low pressure first stage recovery tube 22, a high pressure down range recovery tube 24 and terminal recovery tube 26.

In operation a projectile 28 with integral test specimen 30 is launched down range, accelerated by the light-gas gun 14. With the guidance of the guide track 12 of the instant invention the projectile 28 passes a plurality of vents 32. The launch gases are relieved therethrough and projectile 28 assumes constant free-flight velocity. Projectile 28 continues through the ballistic range 10 containing test environment 16 where the test specimen 30 is exposed to the effects of the environment (e.g., erosion by dust). The projectile 28 then enters the transition to recovery tube 20. During the supersonic phase, a shock precedes the advancing projectile 28 and compresses the air (or other gas) in the transition to recovery tube 20, the first stage recovery tube 22 and the down range recovery tube 24, thereby absorbing kinetic energy and causing projectile 28 to slow down. As projectile 28 slows, the pressure in front of it decreases. Initially there is a pressure differential between the transition to recovery tube 20 and the first stage recovery tube 22 and between the first stage recovery tube 22 and the down range recovery tube 24. These pressure differentials are maintained prior to the arrival of projectile 28 by quick opening valves 34. The opening of the quick opening valves 34 ia synchronized with the projectile motion such that the quick opening valves 34 are opened a few milliseconds prior to projectile arrival. The projectile 28 finally comes to rest in the terminal recovery tube 26.

It is therefore clearly evident that the above operation is dependent upon an accurately dimensioned and aligned projectile guide track 12. Although this track 12 preferably comes in a plurality of track assemblies 18 to be described in detail hereinbelow, the main components of guide track 12 will be described with reference to one such track assembly 18.

Referring to FIG. 2 of the drawing, track assembly 18 is made of a casing 36, preferably of cylindrical configuration, although any other hollow tube like configuration may do. Casing 34 is the main load bearing member and is manufactured from any high strength material such as steel with a precision honed inside diameter 36. Located within casing 34 are a plurality of high strength steel bars or rails 38 which are ground to precision height and width. For optimum projectile guidance four such rails 38 are desirable. Attachment of the four rails 38 to casing 34 is by means of any conventional securing arrangement such as screws 40 inserted through clearance holes 42 in casing 34 from the outside and screwed into tapped holes 44 in rails 38. Inter-rail spacing to the exact outside diameter 46 of projectile 28 is therefore a direct function of the inside diameter 36 of casing 34 and the height H and thickness T of rails 38. By thereby interchanging different sized rails 38 any number of projectiles 28 can be easily accommodated by the instant invention with precision, heretofore, an almost complete impossibility.

Since the track assemblies 18 are limited in length because of limitations in grinding and honing facilities (approximately ten feet) and since the guide rails 12 of recovery systems are in many instances greater than ten feet it is necessary to combine a plurality of rail assemblies 18 to form a complete guide track 12. Reference is now made to FIG. 3 of the drawing which best shows such an arrangement.

Each rail assembly 12 has a precision machined female end section 48 and male end section 50. Female section 48 has an internal edge 52 while male section 50 has an extension 54, both being in precise mating relationship with one another. With such precise machining track assemblies 18 can be brought together in exact alignment and can be rotated to any desired angle.

Once in position, adjacent track assemblies 18 are held together by means of an internally threaded flanged ring 56 screwed on respective externally threaded sections 48 and 50. Each ring 56 has a flanged element 58 formed part thereof and these rings are held together by any conventional securing means such as bolts 60 and nuts 62.

With the instant invention a wide variety of projectiles 28 can be thereby guided through track 12, inexpensively and with complete accuracy and alignment. In addition any length of guide track 12 can be assembled and the various component track assemblies can be rotated to any desired angle.

Although this invention has been described with reference to a particular embodiment it will be understood to those skilled in the art that this invention is also capable of a variety of alternate embodiments within the spirit and scope of the appended claims.

We claim:

1. In a ballistic range of the type utilized for the testing of specimens having a means for propelling a projectile, a projectile guide track and a test environment, the improvement therein being said projectile guide track, said projectile guide track comprising at least one pair of track assemblies, each of said track assemblies having a female end section at one end thereof and a male end section at the other end thereof, each of said end sections having an externally threaded portion thereon, said track assemblies having adjacent male and female end sections in mating relationship with one another, a flanged ring having internal threads thereon engaging each of said externally threaded portions of said track assemblies and means for securing adjacent flanged rings together thereby aligning said track assemblies in a predetermined orientation, said track assemblies being in operative alignment with said propelling means and said test environment, each of said track assemblies being formed of a cylindrical casing having a predetermined internal dimension and four solid, rigid rails circumferentially spaced an equidistance from one another within said casing, each of said rails having means therein for accepting a fastening element, each of said fastening elements allowing for said rail associated therewith to be removably, yet fixedly secureable to said casing and each of said rails being of a precise predetermined height and thickness whereby said projectile propelled by said propelling means remains in proper alignment throughout its passage through said projectile guide track.

2. In a ballistic range as defined in claim 1 wherein each of said rails are securable to said casing by a screw.

3. In a ballistic range as defined in claim 2 wherein said casing and said rails are made of steel.

4. In a ballistic range as defined in claim 3 wherein said means for securing adjacent flanged rings together is in the form of a bolt and nut.

* * * * *